US008894928B2

(12) United States Patent
Haechler (10) Patent No.: US 8,894,928 B2
(45) Date of Patent: Nov. 25, 2014

(54) JUNCTION, DEVICE AND PROCESS FOR TRANSPORTING SAMPLE RACKS

(75) Inventor: Joerg Haechler, Oberwil b. Zug (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 362 days.

(21) Appl. No.: 13/302,160

(22) Filed: Nov. 22, 2011

(65) Prior Publication Data

US 2012/0301358 A1 Nov. 29, 2012

(30) Foreign Application Priority Data

Nov. 23, 2010 (EP) .................................... 10192169

(51) Int. Cl.
| | |
|---|---|
| *G01N 21/00* | (2006.01) |
| *G01N 31/00* | (2006.01) |
| *G01N 33/00* | (2006.01) |
| *G01N 35/02* | (2006.01) |
| *G01N 35/04* | (2006.01) |

(52) U.S. Cl.
CPC ........ *G01N 35/04* (2013.01); *G01N 2035/0467* (2013.01); *G01N 35/026* (2013.01)
USPC ............................................. 422/64; 422/65

(58) Field of Classification Search
USPC ..................................................... 422/64–65
See application file for complete search history.

(56) References Cited

U.S. PATENT DOCUMENTS

| | | | | |
|---|---|---|---|---|
| 5,087,423 | A | * | 2/1992 | Ishibashi .......................... 422/67 |
| 6,080,364 | A | | 6/2000 | Mimura et al. |
| 6,202,829 | B1 | | 3/2001 | Dyke, Jr. et al. |
| 6,520,313 | B1 | * | 2/2003 | Mäkelä et al. ............. 198/369.5 |
| 2008/0069730 | A1 | * | 3/2008 | Itoh ................................. 422/65 |

FOREIGN PATENT DOCUMENTS

| | | |
|---|---|---|
| EP | 1460431 A2 | 2/2004 |
| JP | 09-033539 | 7/1997 |

* cited by examiner

*Primary Examiner* — Jill Warden
*Assistant Examiner* — Julie Tavares
(74) *Attorney, Agent, or Firm* — Dinsmore & Shohl LLP (57) ABSTRACT

A junction for transporting sample racks in an analytical system having one or more work cells for processing samples and a method thereof are disclosed. In one embodiment, the junction may include multiple main transport lines, a turntable and one or more bypass transport lines. The multiple main transport lines can transport first sample racks and second sample racks having different sizes. The rotatable transport line can alternately connect to one or more of the main transport lines. Each of the one or more bypass transport lines can interconnect two of the main transport lines and bypass the turntable. Each of the bypass transport lines can be curved such that transport of the second sample racks through each of the bypass transport lines is enabled and transport of the first sample racks through each of the bypass transport lines is disabled.

20 Claims, 7 Drawing Sheets

JUNCTION, DEVICE AND PROCESS FOR TRANSPORTING SAMPLE RACKS

CROSS REFERENCE TO RELATED APPLICATIONS

The present application claims priority to European Patent Application No. EP10192169.0 filed Nov. 23, 2010.

TECHNICAL FIELD

The present disclosure generally relates to the field of automated analytical sample processing and, more specifically to junctions, devices and processes for transporting sample racks holding sample vessels in a system comprising one or more work cells for processing samples.

BACKGROUND

Automated instruments can be used for analyzing samples with respect to various clinical-chemical and immunochemical analysis items. The instruments may include more than one work cell for performing processing steps. Each of the processing steps can be related to various kinds of analytical methods, and pre-analytical and/or post-analytical processing steps for preparing sample analysis and storing the samples (e.g., for further processing at a later stage).

In the course of automated sample processing, samples or aliquots thereof can be transported from one work cell to another so that individual portions can be withdrawn and/or various fluids such as, for example, reagents, diluents and buffers can be added to the samples. In automated instruments, vessels containing the samples can be transported via sample racks holding the vessels. Specifically, one rack can hold one vessel (single holder) or a plurality of vessels (multiple holders) serially arranged with respect to each other. In automated instruments, a dedicated transporting device can be used for transporting the sample racks between the various work cells. Examples of such transporting devices are described in U.S. Pat. No. 6,202,829 B1 and European Patent Application No. 1460431 A2.

The use of a single rack format (rack size) in the analytical instrument may be limited because different work cells may require different rack formats. Different rack formats may require time consuming and expensive reformatting operations in advance to their use.

Accordingly, alternative devices for transporting sample racks of different formats between various work cells in an analytical instrument may be desired.

SUMMARY

In one embodiment, a junction for transporting sample racks in an analytical system having one or more work cells for processing samples may include multiple main transport lines, a turntable and one or more bypass transport lines. The multiple main transport lines can transport first sample racks and second sample racks. The first sample racks can have a bigger rack size than the second sample racks with respect to transporting directions of the main transport lines. The turntable may include at least one rotatable transport line that transports the first sample racks and the second sample racks. The turntable can be coupled to the main transport lines. The rotatable transport line can alternately connect to one or more of the main transport lines. Each of the one or more bypass transport lines can interconnect two of the main transport lines and bypass the turntable. Each of the bypass transport lines can be curved such that transport of the second sample racks through each of the bypass transport lines is enabled and transport of the first sample racks through each of the bypass transport lines is disabled. The bypass transport lines can be operably coupled to at least one controllable main/bypass line switch that guides the second sample racks from one of the main transport lines to one of the bypass transport lines or keeps the second sample racks on one of the main transport lines.

In another embodiment, an analytical system may include an automated transport device and a controller. The automated transport device can transport first sample racks and second sample racks. The automated transport device may include one or more junctions, a turntable and one or more bypass transport lines. Each of the junctions may include multiple main transport lines that transport the first sample racks and the second sample racks. The first sample racks can have a bigger rack size than the second sample racks with respect to transporting directions of the main transport lines. The turntable may include at least one rotatable transport line that transports the first sample racks and the second sample racks. The turntable can be coupled to the main transport lines. The rotatable transport line can alternately connect to one or more of the main transport lines. Each of the bypass transport lines can interconnect two main transport lines and bypass the turntable. Each of the bypass transport lines can be curved such that the transport of the second sample racks through each of the bypass transport lines is enabled and transport of the first sample racks through each of the bypass transport lines is disabled. The bypass transport lines can be operably coupled to at least one controllable main/bypass line switch that guides the second sample racks from one of the main transport lines to one of the bypass transport lines or keeps the second sample racks on one of the main transport lines. The controller can execute machine readable instructions to control transport of the first sample racks and the second sample racks between two of the main transport lines coupled to the junctions. The rotatable transport line can be rotated to interconnect two or more of the main transport lines. The first sample racks and the second sample racks can be transported by the rotatable transport line. The rotatable transport line can be rotated to alternately connect one or more of the main transport lines. The first sample racks can be transported by the rotatable transport line and the second sample racks can be transported by the bypass transport line that interconnects two or more of the main transport lines.

In yet another embodiment, an automated analytical system may include one or more work cells for processing samples. A method for transporting first sample racks and second sample racks in the automated analytical system may include transporting the first sample racks from a first main transport line to a rotatable transport line. The first sample racks can have a bigger rack size than the second sample racks with respect to a transporting direction. The rotatable transport line can be rotated alternately to connect it to the first main transport line and a second main transport line. The first sample racks can be transported from the rotatable transport line to the second main transport line. The second sample racks can be transported from the first main transport line to the second main transport line via a bypass transport line. The bypass transport line can interconnect the first main transport line and the second main transport line, bypassing the rotatable transport line. The bypass transport line can be curved such that transport of the second sample racks through the bypass transport line is enabled and transport of the first sample racks through the bypass transport lines is disabled It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

As used herein, the term "samples" includes liquid fluids or dry substances in which one or more analytes of interest can be present. In some embodiments, the samples are chemical fluids, which can be subject to one or more chemical analyses and assays such as, but not limited to, drug interaction screening, environmental analysis and identification of organic substances. In some embodiments, the samples can be biological fluids such as body fluids, which include, but are not limited to, blood, serum, urine, saliva and cerebrospinal fluid, which can be subject to one or more analyses and assays in medical and pharmaceutical research and clinical diagnosis.

According to one embodiment, a junction for transporting sample racks in an analytical system may comprise one or more work cells for processing samples. The junction may include plural main transport lines for transporting first and second sample racks. The first sample racks can have a bigger rack size than the second sample racks with respect to a transporting direction of each of the main transport lines. In some embodiments, each of the first sample racks holds plural sample vessels such as, for example, two, three, four, five or more sample vessels, while each of the second sample racks can be limited to holding only one sample vessel.

The junction may further comprise a turntable. The turntable can be provided with at least one rotatable transport line for transporting the first and second sample racks. In the junction, the at least one rotatable transport line can be coupled to the main transport lines. Accordingly, the rotatable transport line can be alternately connected to the main transport lines and/or interconnected with at least two main transport lines.

The junction may further comprise one or more bypass transport lines. Each of the one or more bypass transport lines can interconnect two main transport lines to bypass the turntable and can be curved in a manner to enable transport of the second sample racks and disable transport of the first sample racks. Otherwise, each bypass transport line can be operably coupled with at least one controllable main/bypass line switch. Each controllable main/bypass line switch can guide the second sample racks from one main transport line to the bypass transport line or keep the second sample racks on the main transport line. For example, the controllable main/bypass line switch may include a servo-mechanism operably coupled to a controller that automatically actuates the controllable main/bypass line switch. In some embodiments, the junction comprises one or more bypass transport lines which are arranged adjacent to the turntable. In some embodiments, each bypass transport line can interconnect adjacent main transport lines.

According to the embodiments described herein, each of the transport lines can be configured for transporting the samples racks in one transport direction (one-way) or in both transport directions (both-way).

In some embodiments, the junction may comprise paired main transport lines. Each pair can be configured for transporting the first and second sample racks in opposite transport directions. Specifically, one main transport line can be configured for transporting the sample racks in one transport direction. The second main transport line can be configured for transporting the sample racks in the other transport direction. In some embodiments, the main transport lines of each pair of main transport lines can be configured for transporting the sample racks in both transport directions.

In some embodiments, each of one or more pairs of the main transport lines can be interconnected by at least one interconnection transport line. The interconnection transport line can be operably coupled with at least one controllable main/main line switch. Each of the at least one controllable main/main line switch can guide the second sample racks from one main transport line to the interconnection transport line or keep the first and second sample racks on one main transport line.

In some embodiments, the bypass and interconnection transport lines can form a looped path of travel around the turntable.

In some embodiments, the turntable can be provided with one pair of rotatable transport lines configured for transporting the first and second sample racks in opposite directions.

According to the embodiments described herein, an automated transport device for transporting sample racks in an analytical system can comprise one or more work cells for processing samples. The transport device can include one or more junctions as is described above. The transport device may further include a controller configured to control transporting the sample racks between two main transport lines of one junction according to machine readable instructions. For example, the controller can execute machine readable instructions to rotate the rotatable transport line and interconnect the main transport lines, wherein the first and second sample racks are transported by the rotatable transport line. Alternatively or additionally, the controller can execute machine readable instructions to rotate the rotatable transport line and alternately connect the main transport lines, wherein the first sample racks are transported by the rotatable transport line and the second sample racks are transported by the bypass transport line interconnecting the main transport lines.

In some embodiments, the transport device may comprise paired main transport lines. Each of the main transport lines can be configured for transporting the sample racks in opposite directions. The controller can be configured to control the transport of the sample racks between the main transport lines of one pair of main transport lines. Specifically, the sample racks can be transported from one main transport line to the rotatable transport line by rotating the at least one rotatable transport line to connect with the other main transport line. The sample racks can then be transported to the other main transport line.

Further embodiments of the transport device may include one or more pairs of the main transport lines. Each of the pairs of the main transport lines can be interconnected by at least one interconnection transport line. The interconnection transport line can be operable coupled with at least one controllable main/main line switch. The at least one controllable main/main line switch can guide the second sample racks from one main transport line to the interconnection transport line to transport the second sample racks to another main transport line of the pair of main transport lines or keep the first and second sample racks on one main transport line. For example, the at least one controllable main/main line switch may include a servo-mechanism operably coupled to a controller that automatically actuates the at least one controllable main/main line switch. Furthermore, the controller can be configured to control the transport of the second sample racks between the main transport lines of one pair of main transport lines by transporting the second sample racks by the interconnection line.

In some embodiments of the transport device, one or more of the switches are operatively coupled to a rack size sensor for sensing the rack sizes. Furthermore, the controller can be configured to control the transport of the first and second sample racks based at least in part upon the rack size sensor signals. For example, the rack size can be detected by the rack size sensor and transformed into a rack size-specific sensor signal indicative of the detected rack size. The switches can then be operated based upon the rack-size specific sensor signals. For example, one or more controllers can receive sensor signals and automatically actuate any of the switches (e.g., controllable main/main line switch or controllable main/bypass line switch) operably coupled to the controller based upon the received sensor signals.

According to a yet another embodiment, an analytical system can comprise one or more work cells for processing samples. The work cells can be related to analytical and, optionally, to pre-analytical and/or post-analytical sample processing steps. Furthermore, the system can include an automated transport device as is described above.

In some embodiments, a system may include first and/or second work cells. Each of the first work cells can be operably connected with one auxiliary transport line that is connected to one main transport line for processing samples transported by the auxiliary transport line. Each of the second work cells can be operably connected with at least one main transport line for processing samples transported by the main transport line. In some embodiments, the each of the first work cells is in parallel alignment with one auxiliary transport line.

According to a yet another embodiment, an automated analytical system for transporting first and second sample racks may comprise one or more work cells for processing samples. The first sample racks can have a bigger rack size than the second sample racks with respect to a transporting direction. A method for transporting the first and second sample racks in the automated analytical system may include transporting the first sample racks from one main transport line to another main transport line by rotating at least one rotatable transport line in a manner that alternately connects the transport line to the main transport lines. The second sample racks can be transported from the one main transport line to the other main transport line via a bypass transport line. The bypass transport line can interconnect the main transport lines to bypass the rotatable transport line. The bypass transport line can be curved to enable transport of the second sample racks and disable transport of the first sample racks.

In some embodiments, the first and second sample racks can be transported from one main transport line to another main transport line. The main transport lines can be configured for transporting the sample racks in opposite directions by rotating the at least one rotatable transport line and transporting the sample racks by the rotatable transport line. Specifically, the sample racks can be transported from one main transport line to the rotatable transport line. Then, the at least one rotatable transport line can be rotated to connect the at least one rotatable transport line to the other main transport line. Once connected, the sample racks can be transported to the other main transport line. For example, the at least one rotatable transport line may include a driving means and/or a rotating means operably coupled to one or more controllers. Accordingly, one or more controllers can execute machine readable instructions to automatically cause the at least one rotatable transport line to be actuated.

Figure 1:
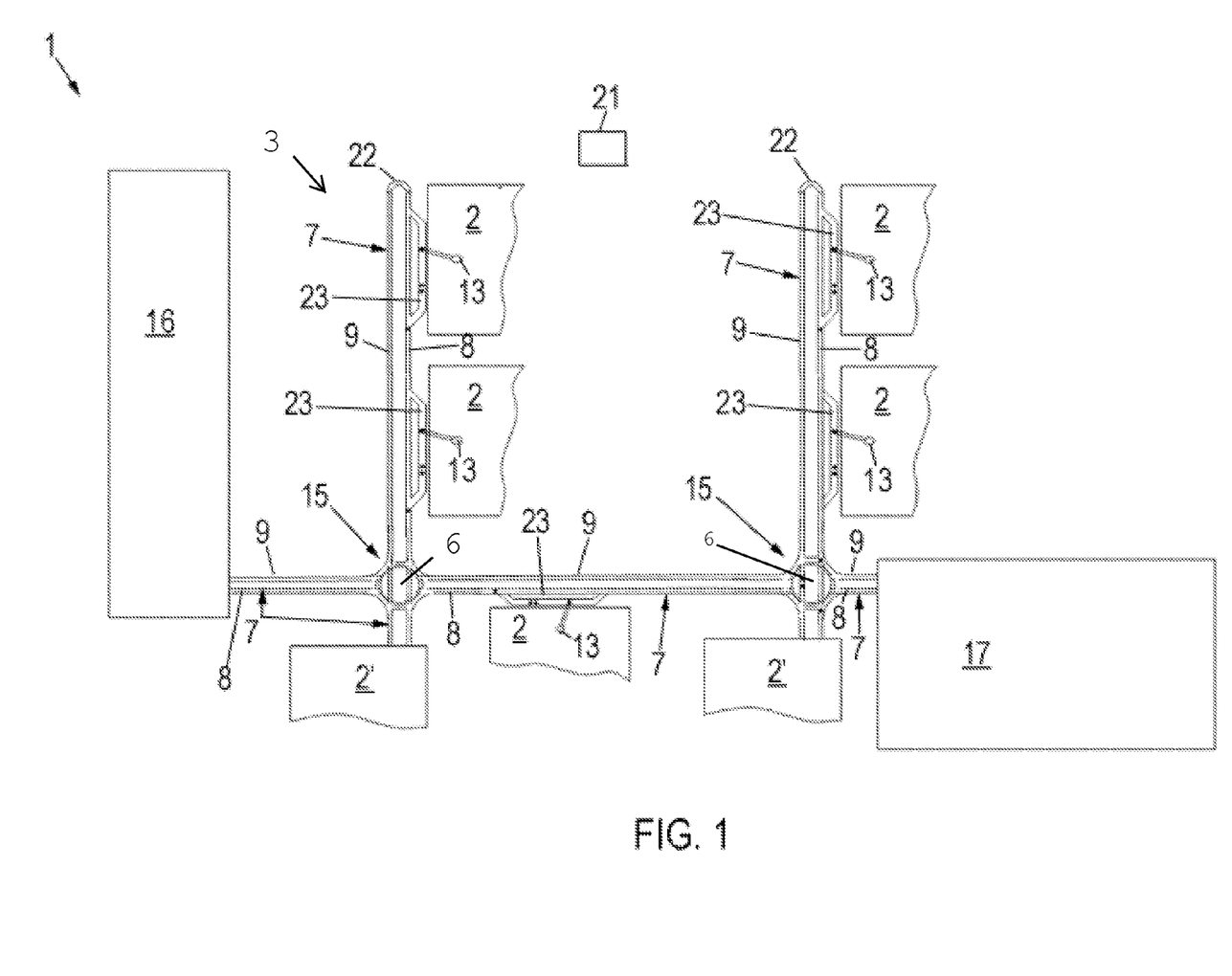
FIG. 1 schematically depicts a top view of a system for processing samples according to one or more embodiments shown and described herein.

Referring now to FIG. 1, an embodiment of a system 1 comprising a plurality of work cells for processing samples is schematically depicted. The system 1 can comprise a plurality of analytical work cells 2, 2', which can be related to one or more kinds of various analytical methods for analyzing samples. The system can further comprise a pre-analytical work cell 16 for performing one or more pre-analytical sample processing steps and a post-analytical work cell 17 for performing one or more post-analytical sample processing steps such as sample storing for later further processing.

Figure 2:
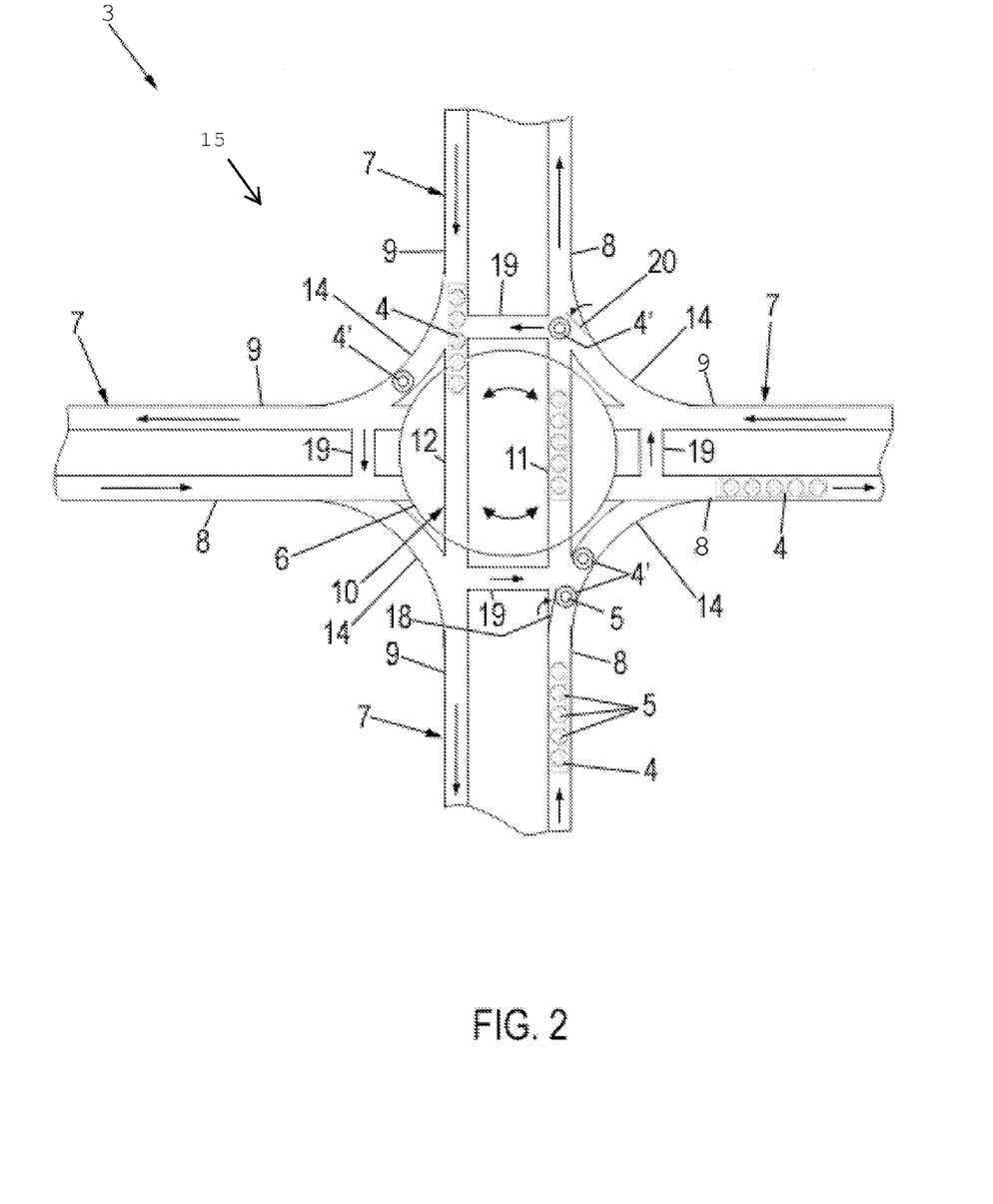
FIG. 2 schematically depicts a top view of a junction of the system of FIG. 1 according to one or more embodiments shown and described herein.
Figure 5:
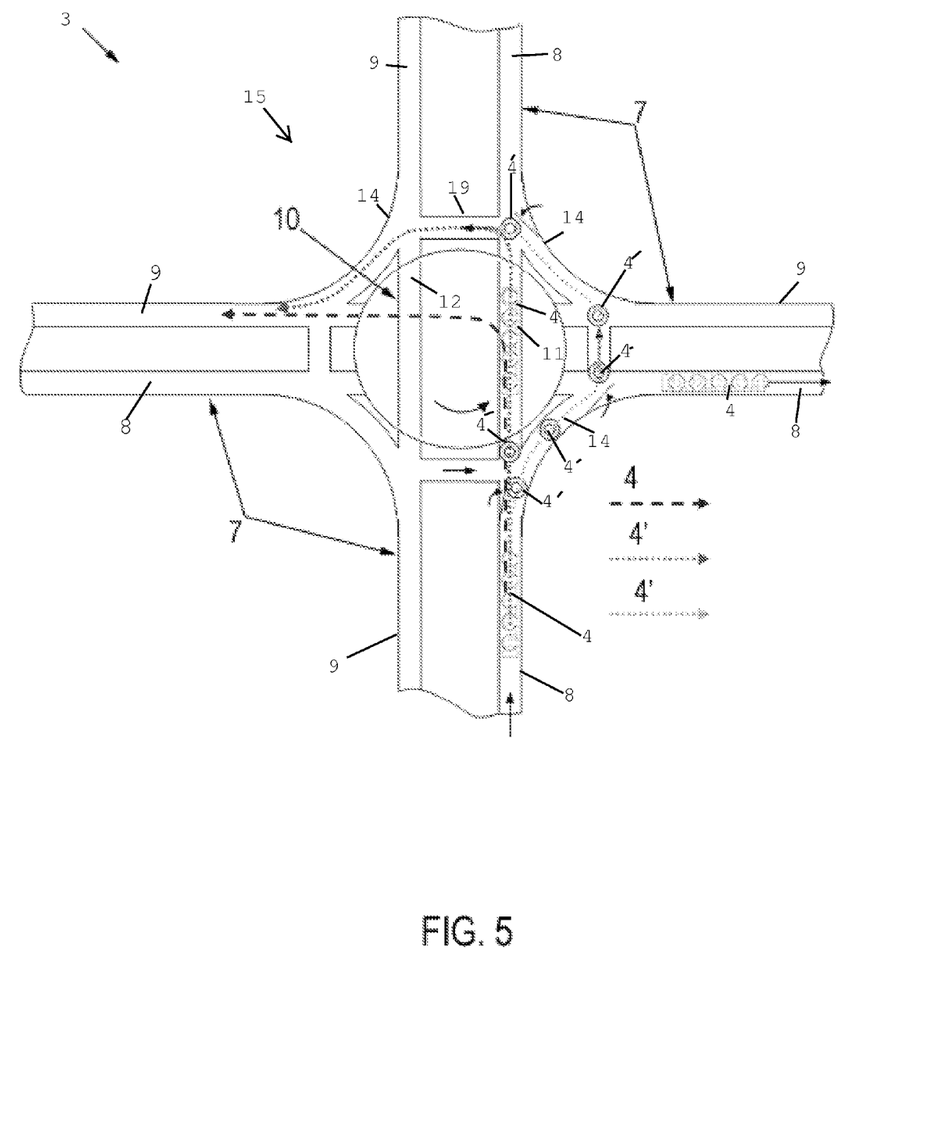

Referring collectively to FIGS. 1 and 2, the system 1 can include a transport device 3 (FIG. 1) comprising a first main transport line 8 and a second main transport line 9 for transporting first sample racks 4 and second sample racks 4'. The first main transport line 8 and the second main transport line 9 may include a driving means and/or a rotating means operably coupled to one or more controllers. Accordingly, one or more controllers can execute machine readable instructions to automatically cause the first main transport line 8 and the second main transport line 9 to be actuated. In some embodiments, the first sample racks 4 and second sample racks 4' can have a different rack format in a generally horizontal plane. Specifically, the transport device 3 can be configured to transport both first and second sample racks 4, 4'. The first sample racks 4 can be a first rack type having a relatively large rack size with respect to transport directions of the first main transport line 8 and the second main transport line 9. The second sample racks 4' can be a second rack type having a relatively small rack size compared to the first rack type. Referring to FIG. 5, each of the sample racks 4, 4' can be provided with one or more sample vessels 5. For example, each of the first sample racks 4 can hold a larger number of sample vessels 5 than the second sample racks 4'. In some embodiments, each of the first sample racks 4 can hold multiple sample vessels 5 such as, but not limited to, five sample vessels 5 while each of the second sample racks 4' can be limited to holding only one sample vessel 5.

Referring collectively to FIGS. 1 and 2, the transport device 3 may include multiple junctions 15 such as, but not limited to, two junctions 15 for transporting the first sample racks 4 and the second sample racks 4' between the first main transport line 8 and the second main transport line 9. Each junction 15 can be coupled to multiple first main transport lines 8 and second main transport lines 9 for transporting first sample racks 4 and second sample racks 4'. Moreover, any portion of the junction 15 can be operably coupled to a controller and the controller can automatically direct operations of the junction 15 by executing machine readable instructions. Each of the first main transport lines 8 and second main transport lines 9 can define a straight path of travel. The first sample racks 4 and second sample racks 4' can move from one point to another without retracing any point of travel, when the first main transport line 8 and second main transport line 9 moves in a single direction. In some embodiments, a first main transport line 8 and second main transport line 9 can be paired into a substantially parallel paths. Accordingly, each pair of main transport lines 7 can include a first main transport line 8 and a second main transport line 9 that are configured to transport the first sample racks 4 and second sample racks 4' in opposite transport directions. For example, each pair of main transport lines 7 may include a first main transport line 8 configured to transport the first sample racks 4 and second sample racks 4' in one transport direction (one-way) and a second main transport line 9 configured to transport the first sample racks 4 and second sample racks 4' in another transport direction (one-way) opposite thereto. Alternatively, each of the first main transport line 8 and the second main transport line 9 can be configured to transport the first sample racks 4 and second sample racks 4' in opposite transport directions (both-way).

Referring still to FIGS. 1 and 2, each junction 15 can comprise a turntable 6 provided with a pair of rotatable transport lines 10. The pair of rotatable transport lines 10 may include a first rotatable transport line 11 and second rotatable transport line 12 for transporting the first sample racks 4 and second sample racks 4' in opposite directions. Specifically, the first rotatable transport line 11 can be configured to transport the first sample racks 4 and second sample racks 4' in one transport direction (one-way) and the second rotatable transport line can be configured to transport the first sample racks 4 and second sample racks 4' in another transport direction (one-way) opposite thereto. Otherwise, each of the first rotatable transport line 11 and the second rotatable transport line 12 can be configured to transport the first sample racks 4 and second sample racks 4' in opposite transport directions (both-way). For example, the turntable 6 may include a driving means and/or a rotating means operably coupled to one or more controllers. Accordingly, one or more controllers can execute machine readable instructions to automatically cause the turntable 6 to be actuated.

The first rotatable transport line 11 and the second rotatable transport line 12 can be coupled to multiple pairs of main transport lines 7. For example, in the embodiment depicted in FIG. 2, four pairs of main transport lines 7. In some embodiments, neighboring pairs of main transport lines 7 can be coupled to a turntable 6 and orthogonally arranged with respect to each other. Specifically, in some embodiments, the junction 15 can be coupled to four pairs of main transport lines 7 with each of the pairs of main transport lines 7 intersecting the junction 15 about 90° from each other. It is noted that, while the pairs of main transport lines 7 are depicted as being offset about 90° in FIGS. 1 and 2, each junction 15 can be coupled to any number of pairs of main transport lines 7 arranged at any angle with respect to one another such as symmetrically arranged or asymmetrically arranged.

Each pair of main transport lines 7 coupled to a turntable 6 can operate as a common transport path for transporting first sample racks 4 and second sample racks 4' towards and away from the turntable 6. Specifically, in some embodiments, each junction 15 can be coupled to a pair of main transport lines 7 comprising a first main transport line 8 and a second main transport line 9. The first main transport line 8 can be operated to transport first sample racks 4 and second sample racks 4' towards the turntable 6 and the second main transport line 9 can be operated to transport first sample racks 4 and second sample racks 4' away from the turntable 6. In some embodiments, a first rotatable transport line 11 of the pair of rotatable transport lines 10 can be coupled to a first main transport line 8 and operated to transport first sample racks 4 and second sample racks 4' in a same direction as the first main transport line 8. A second rotatable transport line 12 of the pair of rotatable transport lines 10 can be coupled to a second main transport line 9 and operated to transport the first sample racks 4 and second sample racks 4' in a same direction as the second main transport line 9.

The turntable 6 can be coupled to the pair of rotatable transport lines 10. Accordingly, the pair of rotatable transport lines 10 can be rotated to connect the first rotatable transport line 11 to any of the first main transport lines 8 adjacent to the turntable 6 and the second rotatable transport line 12 can be rotated to connect to any of the second main transport lines 9 adjacent to the turntable 6. In some embodiments, pairs of main transport lines 7 can be aligned with one another and located adjacent to the turntable such that one pair of rotatable transport lines 10 can connect two pairs of main transport lines 7. Specifically, the first main transport lines 8 can be interconnected by the first rotatable transport line 11 and the second main transport lines 9 can be interconnected by the second rotatable transport line 12.

Moreover, the pair of rotatable transport lines 10 can be rotated to connect the first rotatable transport line 11 to the first main transport line 8 of a pair of main transport lines 7 and the second rotatable transport line 12 to the second main transport line 9 of a pair of main transport lines 7, and can then be rotated by 180° to connect the first rotatable transport line 11 to the second main transport line 9 of the same pair of main transport lines 7 and the second rotatable transport line 12 to the first main transport line 8 the same pair of main transport lines 7.

Referring again to FIG. 1, in some embodiments, one end of the first main transport line 8 and the second main transport lines of a pair of main transport lines 7 can be coupled to a turntable 6 and the other end thereof can be connected by a curved line portion 22. The curved line portion 22 may include a driving means and/or a rotating means operably coupled to one or more controllers. Accordingly, one or more controllers can execute machine readable instructions to automatically cause the curved line portion 22 to be actuated. Accordingly, the second sample racks 4' (FIG. 2) can be conveyed in opposite directions by transporting one-way. In some embodiments, the both ends of the first main transport line 8 and second main transport line 9 of one pair of main transport lines 7 can be connected to a turntable 6. Accordingly, both the first sample racks 4 and second sample racks 4' (FIG. 2) can be conveyed in opposite directions by transporting one-way.

Referring again to FIG. 2, the junction 15 can comprise one or more bypass transport lines 14 arranged adjacent to the turntable 6. Each bypass transport line 14 may include a driving means and/or a rotating means operably coupled to one or more controllers. Accordingly, one or more controllers can execute machine readable instructions to automatically cause each bypass transport line 14 to be actuated. It is noted that, while the embodiment depicted in FIG. 2 includes four bypass transport lines 14, the embodiments described herein may include any number of bypass transport lines 14. Each bypass transport line 14 can be connected to two adjacent pairs of main transport lines 7 that are coupled to a turntable 6. Specifically, each bypass transport line 14 can interconnect the first main transport line 8 of one pair of main transport lines 7 with the second main transport line 9 of an adjacent pair of main transport lines 7. In some embodiments, each bypass transport line 14 can be curved to disable transport of the bigger sized first sample racks 4 and exclusively transport the smaller sized second sample racks 4'. Accordingly, in the junction 15, each bypass transport line 14 can be operated to transport the second sample racks 4' from the first main transport line 8 of one pair of main transport lines 7 to the second main transport line 9 of an adjacent pair of main transport lines 7.

In some embodiments, each bypass transport line 14 is operably coupled to one controllable main/bypass line switch 18 operable to guide the second sample racks 4' from the first main transport line 8 of the one pair of main transport lines 7 to the bypass transport line 14 connected thereto or to keep the second sample racks 4' on the first main transport line 8 for transport towards the turntable 6. While not depicted in the figures, in some embodiments, the controllable main/bypass line switch 18 can be operably coupled to a rack size sensor configured for sensing the rack sizes so as to obtain rack size-specific sensor signals. Control of the controllable main/bypass line switch 18 can be based on the rack size-specific sensor signals. For example, the controllable main/bypass line switch 18 may include a servo-mechanism that is operably coupled to a controller and the controller can actuate the controllable main/bypass line switch 18 automatically by executing machine readable instructions.

In some embodiments, the first main transport line 8 and second main transport line 9 of one pair of main transport lines 7 can be interconnected by an interconnection transport line 19 arranged adjacent to the turntable 6. The interconnection transport line 19 can be configured for transporting the second sample racks 4'. Each interconnection transport line 19 may include a driving means and/or a rotating means operably coupled to one or more controllers. Accordingly, one or more controllers can execute machine readable instructions to automatically cause each interconnection transport line 19 to be actuated. The interconnection transport line 19 can be operably coupled to a controllable main/main line switch 20 operable to guide the second sample racks 4' from the first main transport line 8 and/or second main transport line 9 to the interconnection transport line 19 or to keep the first sample racks 4 and second sample racks 4' on the first main transport line 8 and/or second main transport line 9. For example, the controllable main/main line switch 20 may include a servo-mechanism that is operably coupled to a controller and the controller can actuate the controllable main/main line switch 20 automatically by executing machine readable instructions. While not depicted in the figures, in some embodiments, the controllable main/main line switch 20 can be operably coupled to a rack size sensor configured for sensing the rack sizes so as to obtain rack size-specific sensor signals. Control of the controllable main/main line switch 20 can be based upon the rack size-specific sensor signals.

Referring still to FIG. 2, the first main transport line 8 and second main transport line 9 of each pair of main transport lines 7 can be interconnected by bypass transport lines 14. Moreover, interconnection transport lines 19 can interconnect the first main transport lines 8 and second main transport lines 9 of each pair of main transport lines 7. Thus, the bypass transport lines 14 and interconnection transport lines 19 can form a looped path of travel around the turntable 6. Accordingly, the second sample racks 4' can be transported on a looped travel path around the turntable 6 permitting the second sample racks 4' to repeat the path of travel as often as needed when moving in one-way.

Figure 6:
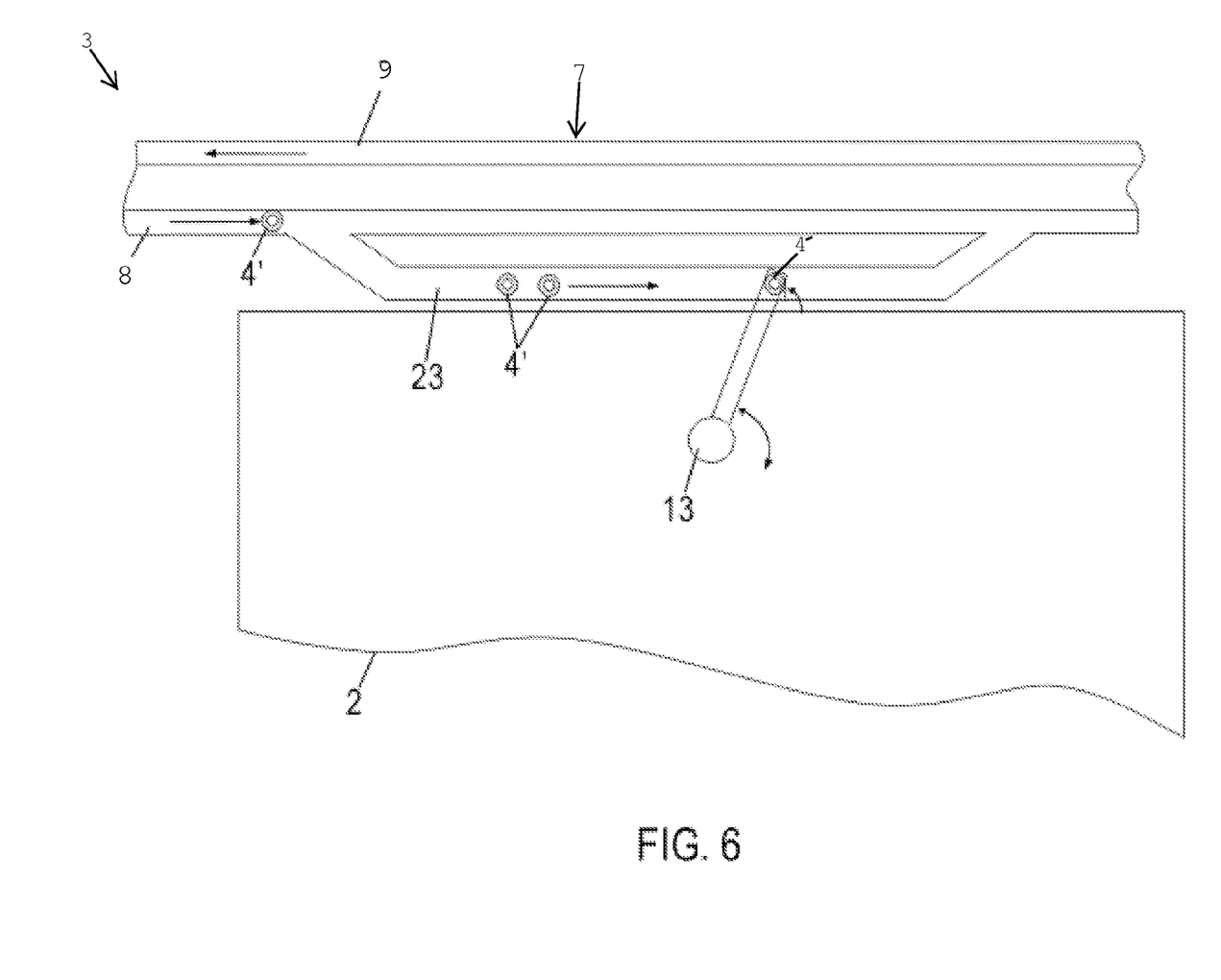
FIG. 6 schematically depicts a top view of a first work cell of the system of FIG. 1 according to one or more embodiments shown and described herein.

Referring again to FIG. 1, the transport device 3 can include one or more auxiliary transport lines 23. Each of the one or more auxiliary transport lines 23 can be connected and provided in parallel alignment to a first main transport line 8 and/or a second main transport line 9 configured for transporting the second sample racks 4' in one-way. Referring now to FIG. 6, in some embodiments, each auxiliary transport line 23 can be connected to the first main transport line 8 of one pair of main transport lines 7 so that second sample racks 4' can be transported away from the turntable 6 (FIG. 1) by the auxiliary transport line 23. In some embodiments, each auxiliary transport line 23 can be operatively coupled to one controllable main/auxiliary line switch (not depicted in FIG. 6) operable to guide second sample racks 4' from the first main transport line 8 to the auxiliary transport line 23 or to keep the second sample racks 4' on the first main transport line 8. From the auxiliary transport line 23, second sample racks 4' can be transported back to the first main transport line 8.

In some embodiments, each auxiliary transport line 23 can be associated with one or more first analytical work cells 2. The first analytical work cells 2 can be related to processing steps that analyze samples contained in the second sample racks 4'. Specifically, the first analytical work cells 2 can be used for processing samples simultaneously with transporting the second sample racks 4' through the auxiliary transport line 23 associated therewith. The first analytical work cells 2 can be configured to perform sample processing operations such as, but not limited to, pipetting operations by means of a pipetting device 13 adapted for withdrawing sample portions, e.g., for analysis thereof, and/or adding fluidic substances to the samples such as diluents, buffers or any other similar substance. When transported by the auxiliary transport line 23, second sample racks 4' can have a transport speed smaller than a transport speed when transported by the first main transport line 8 connected thereto. In some embodiments, second samples racks 4' conveyed by the auxiliary transport line 23 can also be stopped for a predetermined time interval for performing sample processing operations. While not illustrated, in some embodiments, the first analytical work cells 2 are related to processing steps configured for analyzing samples contained in either the first sample racks 4 (FIG. 2) or the second sample racks 4'. Accordingly, the auxiliary transport lines 23 can be configured for transporting both the first sample racks 4 (FIG. 2) and second sample racks 4' in one-way and the controllable main/auxiliary line switches (not illustrated) can be operable to guide the first sample racks 4 (FIG. 2) and second sample racks 4' from the first main transport line 8 to the auxiliary transport line 23 or to keep the first sample racks 4 (FIG. 2) and second sample racks 4' on the first main transport line 8.

Figure 7:
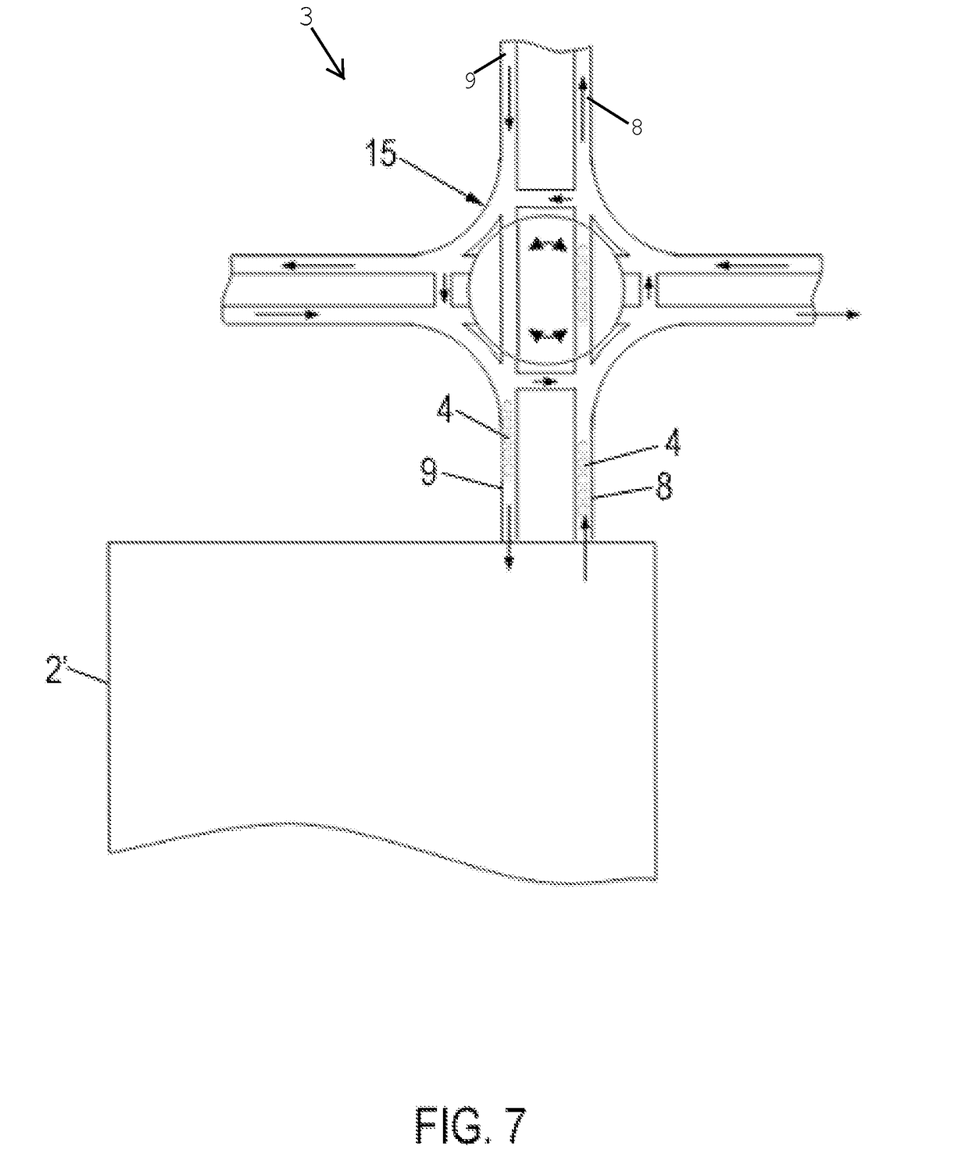
FIG. 7 schematically depicts a top view of a second work cell of the system of FIG. 1 according to one or more embodiments shown and described herein.

Referring now to FIG. 7, the first main transport line 8 and second main transport line 9 of one or more pairs of main transport lines 7 can be associated with a second analytical work cell 2'. The second analytical work cells 2' can be related to processing steps configured for analyzing the samples transported by the first sample racks 4. The second analytical work cell 2' can be used for processing the samples simultaneously with transporting the first sample racks 4 containing the samples by the pair of main transport lines 7 associated therewith. One pair of main transport lines 7 can be associated with one second analytical work cell 2' and the first main transport line 8 and second main transport line 9 can be directed into the second analytical work cell 2'. Accordingly, first sample racks 4 can be transported in and out the second analytical work cell 2'. While not depicted in FIG. 7, in some embodiments, the first analytical work cells 2 can be related to processing steps that analyze samples contained in the first sample racks 4 and/or the second sample racks 4'.

Referring back to FIG. 1, the transport device 3 of the system 1 can be driven by one or more driving means such as, but not limited to, a belt drive. In some embodiments, individual transport lines are driven by a separate driving means. In further embodiments, one or more transport lines are driven by a same driving means. In some embodiments, each rotatable transport line can be rotated by one rotating means such as, but not limited to, an electrically driven rotor. As is described in further detail herein, each of the driving means and/or the rotating means can be operably coupled to a controller. Accordingly, one or more controllers can execute machine readable instructions to automatically cause any of the transport lines to be actuated, as described herein.

Figure 3:
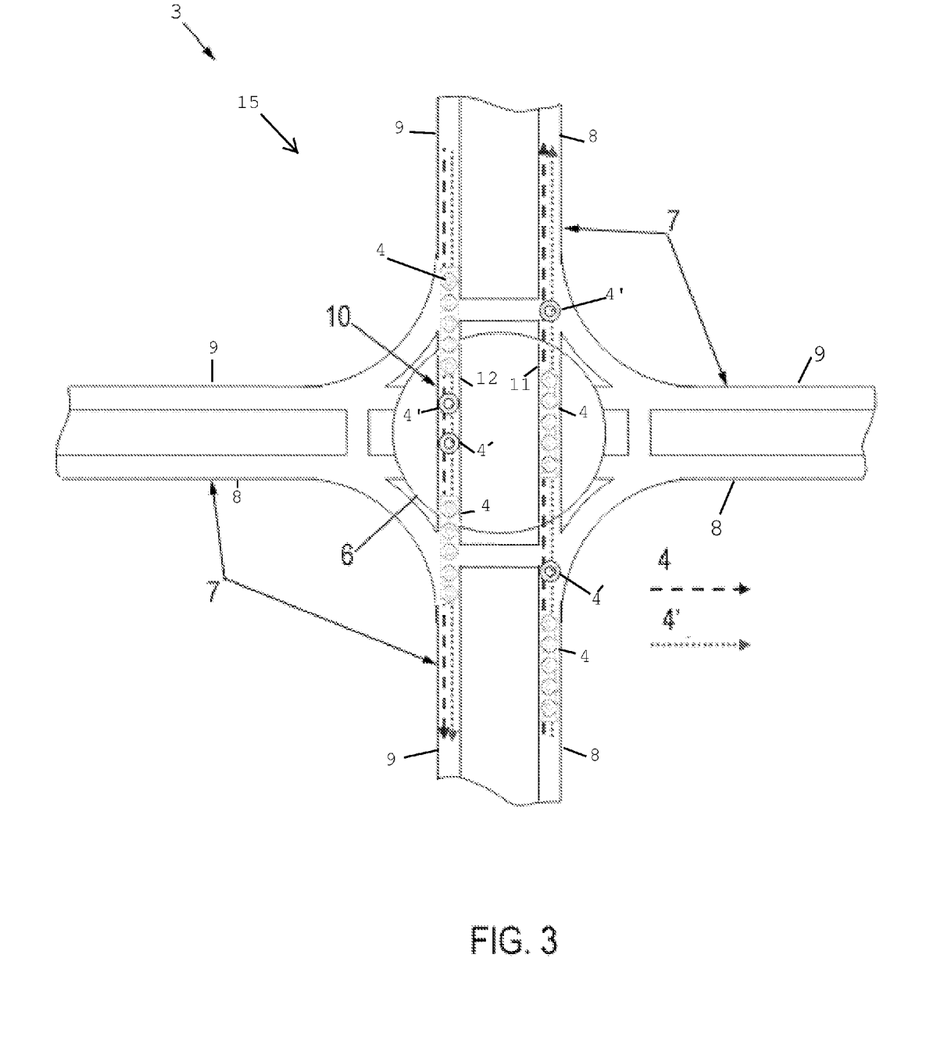
FIGS. 3-5 schematically depict top views of sample racks in transit using a junction according to one or more embodiments shown and described herein.
Figure 4:
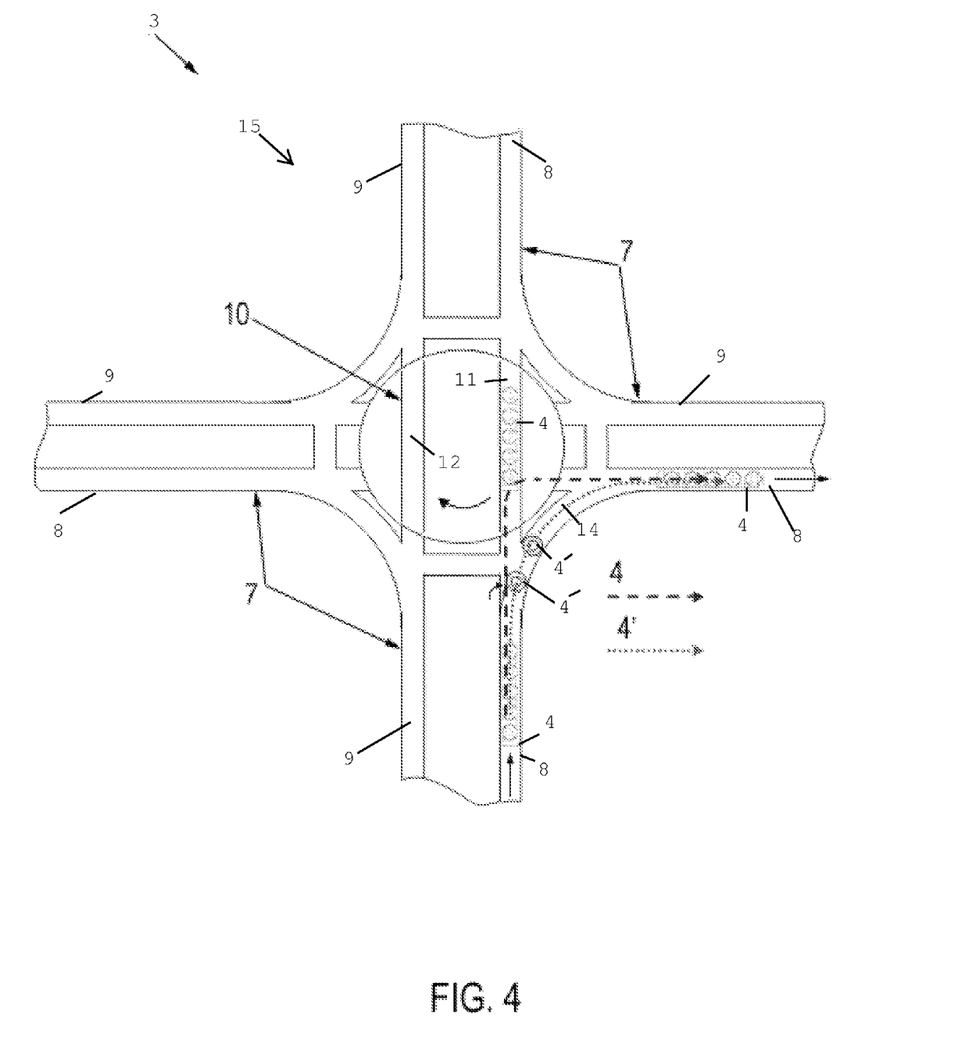

The system 1 may further comprise a controller 21 operable to automatically control sample processing by the first analytical work cells 2, the second analytical work cell 2', the pre-analytical work cell 16, the post-analytical work cell 17, or combinations thereof. The controller may also control transport of the first sample racks 4 and second sample racks 4' via the transport device 3. The controller 21 can, e.g., be embodied as programmable logic controller running a computer-readable program electrically connected to the system components which require control and/or provide information which include the first analytical work cells 2, the second analytical work cell 2', the pre-analytical work cell 16, the post-analytical work cell 17 and the transport device 3 (including the various transport lines and switches). Specifically, in some embodiments, the controller 21 is configured to execute machine readable instructions to control automatically the various scenarios for transporting first sample racks 4 and second sample racks 4' by controlling automatically the junctions 15, as schematically depicted in FIGS. 3 to 5. Accordingly, the embodiments described hereinafter can be implemented as machine readable instructions that can be automatically executed by the controller 21.

Referring now to FIG. 3, the transport of first sample racks 4 and second sample racks 4' via a junction 15 is schematically depicted. The first sample racks 4 and second sample racks 4' can be transported from a lower pair of main transport lines 7 to an upper pair of main transport lines 7. The pair of rotatable transport lines 10 can be rotated to interconnect the first main transport lines 8 and second main transport lines 9 of one set of opposing pairs of main transport lines 7 via the first rotatable transport line 11 and second rotatable transport lines 12, respectively. The first sample racks 4 and second sample racks 4' can then be transported passing the turntable 6 in a straight path of travel (the path of the first sample racks 4 is generally indicated in FIG. 3 by dashed arrows and the path of the second sample racks 4' is generally indicated in FIG. 3 by the dotted arrows). Accordingly, when the turntable 6 has been brought in a rotational position to interconnect two opposing pairs of main transport lines 7, it is not required to further rotate the turntable 6 to transport the first sample racks 4 and second sample racks 4' from the one pair of main transport lines 7 to the other pair of main transport lines 7.

Referring now to FIG. 4, the transport of first sample racks 4 and second sample racks 4' via a junction 15 is schematically depicted. The first sample racks 4 and second sample racks 4' can be transported from a lower pair of main transport lines 7 to the adjacent right pair of main transport lines 7. Accordingly, the transport direction of the first sample racks 4 and second sample racks 4' can be directed to the right. Specifically, the turntable 6 can be rotated to alternately connect to two pairs of main transport lines. For example, the turntable 6 can be rotated to a first rotational position, where the first rotatable transport line 11 and second rotatable transport line 12 are connected to the first main transport line 8 and second main transport line 9 of the lower pair of main transport lines 7. One or more first sample racks 4 can then be transported from the first main transport line 8 to the first rotatable transport line 11 and stopped on the turntable 6. The turntable 6 can then be rotated to a second rotational position that is a 90° turn to the right from the first rotational position, where the first rotatable transport line 11 and second rotatable transport line 12 are connected to the first main transport line 8 and second main transport line 9 of the right pair of main transport lines 7. The one or more first sample racks 4 can then be transported from the first rotatable transport line 11 to the first main transport line 8 of the right pair of main transport lines 7. The path of the first sample racks 4 is generally indicated in FIG. 4 by the dashed arrow. The second sample racks 4', instead of being transported by the turntable 6, can be transported via the bypass transport line 14 that interconnects the first main transport lines 8 of the lower pair of main transport lines 7 and the pair of main transport lines 7 (the path of the second sample racks 4' is generally indicated in FIG. 4 by the dotted arrow). Accordingly, the turntable 6 can be rotated to transport the first sample racks 4 from one first main transport line 8 to another first main transport line 8, while the second sample racks 4' can be transported via the bypass transport line 14.

Referring now to FIG. 5, the transport of first sample racks 4 and second sample racks 4' via a junction 15 is schematically depicted. The first sample racks 4 and second sample racks 4' can be transported from a lower pair of main transport lines 7 to an adjacent left pair of main transport lines 7. Accordingly, the transport direction of the first sample racks 4 and the second sample racks 4' can be changed to the left. Thus, the turntable 6 can be rotated to alternately connect two pairs of main transport lines 7. Specifically, the turntable 6 can be rotated to a first rotational position, where the first rotatable transport line 11 and second rotatable transport line 12 are connected to the first main transport line 8 and second main transport line 9 of the lower pair of main transport lines 7. One or more first sample racks 4 can then be transported from the first main transport line 8 to the first rotatable transport line 11 and stopped on the turntable 6. The turntable 6 can then be rotated to a third rotational position that is a 90° turn to the left of the first rotational position, where the first rotatable transport line 11 and second rotatable transport line 12 are connected to the first main transport line 8 and second main transport line 9 of the left pair of main transport lines 7. The one or more first sample racks 4 can then be transported from the first rotatable transport line 11 to the second main transport line 9 of the left pair of main transport lines 7. The transport of the first sample racks 4 is generally indicated by the dashed arrow in FIG. 5. The turntable 6 can be rotated to the first rotational position, where the first rotatable transport line 11 and second rotatable transport line 12 interconnect the first main transport lines 8 and second main transport lines 9 of opposing upper and lower pairs of main transport lines 7, to transport the second sample racks 4'. The second sample racks 4' can then be transported from the first main transport line 8 of the lower pair of main transport lines 7 to the first main transport line 8 of the upper pair of main transport lines 7 in a straight path of travel through the turntable 6. The second sample racks 4' can then be transported from the first main transport line 8 via the interconnection transport line 19 to the second main transport line 9 of the upper pair of main transport lines 7. Then, the second sample racks 4' can be transported from the second main transport line 9 of the upper pair of main transport lines 7 to second main transport line 9 of the left pair of main transport lines 7 via the bypass transport line 14 that interconnects the second main transport line 9 of the upper pair of main transport lines 7 and the second main transport line 9 of the left pair of main transport lines 7 (the path of the second sample racks 4', described immediately above, is generally indicated in FIG. 5 by the dark dotted arrow). Instead of being transported via the turntable 6, the second sample racks 4' can also be transported using a combined path of travel that includes the bypass transport line 14 that interconnects the first main transport line 8 of the lower pair of main transport lines 7 and the first main transport line 8 of the right pair of main transport lines 7, the interconnection transport line 19 of the right pair of main transport lines 7, the bypass transport line 14 that interconnects the second main transport line 9 of the right pair of main transport lines 7 and the first main transport line 8 of the upper pair of main transport lines 7, the interconnection transport line 19 of the upper pair of main transport lines 7, and the bypass transport line 14 that interconnects the second main transport line 9 of the upper pair of main transport lines 7 and the second main transport line 9 of the left pair of main transport lines 7 (the path of the second sample racks 4' that bypasses the turntable is generally indicated in FIG. 5 by the lighter dotted arrow).

It is noted that, while specific scenarios are depicted in FIGS. 3-5, the turntable 6 can be rotated automatically by the controller 21 in any direction and by any amount to transport first sample racks 4 and second sample racks 4'. For example, the turntable 6 can be rotated to connect the first rotatable transport lines 11 and second rotatable transport line 12 to the first main transport line 8 and second main transport line 9, respectively, of a pair of main transport lines 7. One or more first sample racks 4 and/or second sample racks 4' can then be transported from the first main transport line 8 thereof to the first rotatable transport line 11 and stopped on the turntable 6. The turntable 6 can then be rotated to another rotational position by 180°, where the first rotatable transport line 11 is connected to the second main transport line 9 of the same pair of main transport lines 7 and the second rotatable transport line 12 is connected to the first main transport line 8 of the same pair of main transport lines 7. Accordingly, the turntable can be utilized to transport the first sample racks 4 and/or second sample racks 4' between the first main transport line 8 and the second main transport line 9 of a pair of main transport lines 7. It is noted that the terms "first" and "second" are provided herein for clarity and not by way of limitation. Accordingly, operations performed by the "first" can alternatively or additionally be performed by the "second" without departing from the scope of the present disclosure.

Referring collectively to FIGS. 1 and 2, the system 1 can include a transport device 3 for the transport of first sample racks 4 and second sample racks 4' that have different rack formats. It is noted that, while first sample racks 4 are depicted as multiple holders (multi-vessel racks) and second sample racks 4' are depicted as single holders (one-vessel racks) in FIG. 2, the embodiments described herein may find favorable utility for transporting sample racks having varied sizes between any of the pre-analytical work cells 16, first analytical work cells 2, second analytical work cells 2' and post-analytical work cells 17. The bypass transport lines 14 and the junctions 15 can be used for the transport of first sample racks 4 and second sample racks 4'. Specifically, when travelling along a straight path of travel, first sample racks 4 and second sample racks 4' can be transported on the same first main transport line 8 or second main transport line 9. If first sample racks 4 and/or second sample racks 4' have to turn to the direction of the first main transport line 8, the junction 15 can be used. Specifically, the first sample racks 4 can be transported via the turntable 6 and the second sample racks 4' can be transported via the bypass transport line 14, as described herein. Accordingly, the second sample racks 4' can be diverted before reaching the turntable 6 and can change direction via the bypass transport line 14, which can be curved and can connect with the second main transport line 9 coming from the turntable 6. When entering the second main transport line 9, either the first sample racks 4 or second sample racks 4' can be held back to avoid sample rack collision. Transfer of the second sample racks 4' via the bypass transport line 14 can be more efficient than via the turntable 6. For example, when two second sample racks 4' are following a first sample rack 4, the turntable 6 may require multiple operations to transport each of the second sample racks 4'. When first sample racks 4 and/or second sample racks 4' have to turn away from the first main transport line 8, the junction 15 can be used. The first sample racks 4 can be transported via the turntable 6 and the second sample racks 4' can pass the turntable 6 in a straight path of travel, and then can be pushed to the interconnection transport line 19 of another pair of main transport lines 7 and the bypass transport line 14 can connect with the second main transport line 9 coming from the turntable 6. Alternatively, when the turntable 6 is occupied, the second sample racks 4' can be transported around the turntable 6 instead of waiting until the turntable 6 is unoccupied.

In some embodiments, an identity of first sample racks 4 and/or second sample racks 4' can be read by means of a reader such as, but not limited to, an RFID-reader when first sample racks 4 and/or second sample racks 4' approach a junction 15. Moreover, the reader can be operably coupled to the controller 21. Accordingly, transport of first sample racks 4 and/or second sample racks can be automated based upon rack type. For example, second sample racks 4' can be transported by passing the turntable 6 in a straight line of travel or via one or more bypass transport lines 14 bypassing the turntable 6.

In some embodiments, the second sample racks 4' can be transported to the auxiliary transport lines 23 for analysis by the first analytical work cells 2. The first analytical work cells 2 can, for example, be related to a "pick-in-space" method for pipetting samples contained in the second sample racks 4'. In some embodiments, before being transported to the pipetting position, an identity of the second sample racks 4' can be read by means of a reader such as, but not limited to, an RFID-reader to control pipetting of the samples contained. When in the pipetting position, specific mechanical positioning means can position the second sample racks 4' appropriately to enable precise pipetting operations. When being configured for processing samples contained in first sample racks 4, the first sample racks 4 holding plural sample vessels 5 can be moved stepwise through the pipetting position so that pipetting at every sample position in the first sample rack 4 can be performed.

In the system 1, a process flow can be implemented as machine readable instructions that are executed by the controller 21. The process flow can include pre-analytical, analytical and post-analytical sample processing steps can be based on various parameters such as, but not limited to, assigned test requests, information about the vessel type, system status information and the like. Specifically, in the pre-analytical work cell 16, samples can be processed by conventional processing operations such as centrifugation, de-capping, aliquoting and the like. After finishing pre-analytical processing steps, samples can be placed in sample vessels 5 of the first sample racks 4 and second sample racks 4'. The first sample racks 4 and second sample racks 4' can then be transported to one or more of the first analytical work cells 2 and second analytical work cells 2' by the transport device 3, which can include multiple pairs of main transport lines 7. Each pair of main transport lines 7 can include a first main transport line 8 and second main transport line 9 that run in opposite directions and are substantially parallel. In some embodiments, the transport device 3 can be implemented as right-hand traffic system (i.e., racks keep to the right side of each pair of main transport lines). After analyzing the samples, the first sample racks 4 and second sample racks 4' can be transported to the post-analytical work cells 17, e.g., for storing the samples for further processing or discharging.

In the system 1, the junctions 15 can allow for an efficient change of transport direction of both first sample racks 4 and second sample racks 4' with relatively low space requirements. Moreover, the system 1 can operate with first sample racks 4 and second sample racks 4' having different rack sizes without having to reformat settings of the system 1 to adapt to the different rack sizes. Accordingly, costs, time and space for reformatting the system 1 can be avoided. Accordingly the embodiments described herein can utilize the flexibility provided when samples are transported in small-sized sample racks such single holders and, at the same time, provide an efficient way for transporting bigger-sized sample racks, which can be targeted for specific work cells.

It should now be understood that the embodiments described herein relate to junctions for transporting sample racks throughout a system having one or more work cells for processing samples. The system may include multiple main transport lines for transporting first and second sample racks. The first sample racks can have a bigger rack size than the second sample racks with respect to transporting directions of the main transport lines. A turntable can be provided with at least one rotatable transport line for transporting the sample racks. The rotatable transport line can be coupled to the main transport lines and alternately connect the rotatable transport line to the main transport lines and/or to interconnect at least two main transport lines. Each of one or more bypass transport lines can interconnect two main transport lines and bypass the turntable. Each bypass transport line can be curved to enable transport of the second sample racks and disable transport of the first sample racks. Each bypass transport line can be associated with at least one controllable main/bypass line switch that is operable to guide the second sample racks from one main transport line to the bypass transport line or to keep the second sample racks on the main transport line. The embodiments described herein further relate to a system having an automated transport device that may include one or more junctions. Further embodiments relate to a process for transporting the first and second sample racks. The process may include transporting the first sample racks from one main transport line to another main transport line by rotating at least one rotatable transport line in a manner to alternately connect it to the main transport lines. The second sample racks can be transported from the one main transport line to another main transport line by a bypass transport line. The bypass transport line interconnecting the main transport lines can bypass the rotatable transport line and can be curved to enable transport of the second sample racks and disable transport of the first sample racks.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and the scope of the claimed subject matter. Thus it is intended that the specification cover the modifications and variations of the various embodiments described herein provided such modifications and variations come within the scope of the appended claims and their equivalents.

What is claimed is:

1. A junction for transporting sample racks in an analytical system having one or more work cells for processing samples, the junction comprising:
    multiple main transport lines that transport first sample racks and second sample racks, wherein the first sample racks have a bigger rack size than the second sample racks with respect to transporting directions of the main transport lines;
    a turntable comprising at least one rotatable transport line that transports the first sample racks and the second sample racks, wherein the turntable is coupled to the main transport lines and the rotatable transport line alternately connects to one or more of the main transport lines;
    one or more bypass transport lines, wherein each of the bypass transport lines interconnect two of the main transport lines and bypass the turntable and each of the bypass transport lines is curved such that transport of the second sample racks through each of the bypass transport lines is enabled and transport of the first sample racks through each of the bypass transport lines is disabled, and wherein the bypass transport lines are operably coupled to at least one controllable main/bypass line switch that guides the second sample racks from one of the main transport lines to one of the bypass transport lines or keeps the second sample racks on one of the main transport lines; and
    a controller that executes machine readable instructions to control transport of the first sample racks and the second sample racks between the two of the main transport lines, wherein the controller is operably coupled to a rack size sensor that detects rack sizes and provides rack size specific sensor signals indicative of the rack sizes, and the controller executes the machine readable instructions to operate the controllable main/bypass line switch based upon the rack size specific sensor signals.

2. The junction according to claim 1, wherein the bypass transport lines are located adjacent to the turntable.

3. The junction according to claim 1, wherein each of the bypass transport lines interconnects adjacent main transport lines.

4. The junction according to claim 1, wherein the main transport lines comprise one or more pairs of main transport lines, wherein each of the pairs of main transport lines comprises a first main transport line that transports the first sample racks and the second sample racks in a first direction and a second main transport line that transports the first sample racks and the second sample racks in an opposite direction to the first direction.

5. The junction according to claim 4, further comprising an interconnection transport line that interconnects the first main transport line and the second main transport line, wherein the interconnection transport line is operably coupled to at least one controllable main/main line switch that guides the second sample racks from the first main transport line to the second main transport line via the interconnection transport line or keeps the first sample racks and the second sample racks on the first main transport line or the second main transport line.

6. The junction according to claim 5, wherein the bypass transport lines and the interconnection transport line form a looped path of travel around the turntable.

7. The junction according to claim 1, wherein the turntable comprises a first rotatable transport line that transports the first sample racks and the second sample racks in a first direction and a second rotatable transport line that transports the first sample racks and the second sample racks in a direction opposite to the first direction.

8. The junction according to claim 1, wherein the main transport lines comprise one or more pairs of main transport lines, wherein each of the pairs of main transport lines comprises a first main transport line that transports the first sample racks and the second sample racks in a first direction and a second main transport line that transports the first sample racks and the second sample racks in an opposite direction to the first direction, and wherein the controller executes the machine readable instructions to rotate the rotatable transport line and transport the first sample racks and the second sample racks via the rotatable transport line.

9. The junction according to claim 8, further comprising an interconnection transport line that interconnects the first main transport line and the second main transport line, wherein the interconnection transport line is operably coupled to at least one controllable main/main line switch that guides the second sample racks from the first main transport line to the second main transport line via the interconnection transport line or to keeps the first sample racks and the second sample racks on the main transport lines, wherein the controller executes the machine readable instructions to transport the second sample racks between the first main transport line and second main transport line via the interconnection transport line.

10. An analytical system comprising:
an automated transport device for transporting first sample racks and second sample racks, the automated transport device comprising:
one or more junctions, wherein each of the junctions comprises multiple main transport lines that transport the first sample racks and the second sample racks and the first sample racks have a bigger rack size than the second sample racks with respect to transporting directions of the main transport lines;
a turntable comprising at least one rotatable transport line that transports the first sample racks and the second sample racks, wherein the turntable is coupled to the main transport lines and the rotatable transport line alternately connects to one or more of the main transport lines; and
one or more bypass transport lines, wherein each of the bypass transport lines interconnect two main transport lines and bypass the turntable and each of the bypass transport lines is curved such that the transport of the second sample racks through each of the bypass transport lines is enabled and transport of the first sample racks through each of the bypass transport lines is disabled and wherein the bypass transport lines are operably coupled to at least one controllable main/bypass line switch that guides the second sample racks from one of the main transport lines to one of the bypass transport lines or keeps the second sample racks on one of the main transport lines; and
a controller that executes machine readable instructions to control transport of the first sample racks and the second sample racks between two of the main transport lines coupled to the junctions such that:

the rotatable transport line is rotated to interconnect two or more of the main transport lines, wherein the first sample racks and the second sample racks are transported by the rotatable transport line; or
the rotatable transport line is rotated to alternately connect one or more of the main transport lines, wherein the first sample racks are transported by the rotatable transport line and the second sample racks are transported by the bypass transport line that interconnects two or more of the main transport lines,
wherein the controller is operably coupled to a rack size sensor that detects rack sizes and provides rack size specific sensor signals indicative of the rack sizes, and the controller executes the machine readable instructions to operate the controllable main/bypass line switch based upon the rack size specific sensor signals.

11. The analytical system according to claim 10, wherein the main transport lines comprise one or more pairs of main transport lines, wherein each of the pairs of main transport lines comprises a first main transport line that transports the first sample racks and the second sample racks in a first direction and a second main transport line that transports the first sample racks and the second sample racks in an opposite direction to the first direction, and wherein the controller executes the machine readable instructions to rotate the rotatable transport line and transport the first sample racks and the second sample racks via the rotatable transport line.

12. The analytical system according to claim 11, further comprising an interconnection transport line that interconnects the first main transport line and the second main transport line, wherein the interconnection transport line is operably coupled to at least one controllable main/main line switch that guides the second sample racks from the first main transport line to the second main transport line via the interconnection transport line or to keeps the first sample racks and the second sample racks on the main transport lines, wherein the controller executes the machine readable instructions to transport the second sample racks between the first main transport line and second main transport line via the interconnection transport line.

13. The analytical system according to claim 10, further comprising one or more work cells for processing samples, wherein the automated transport device transports the first sample racks and the second sample racks between the work cells.

14. The analytical system according to claim 13, wherein the work cells comprise a first work cell and a second work cell, wherein the first work cell is operably coupled with an auxiliary transport line connected to the main transport lines for processing samples transported by the auxiliary transport line, and the second work cell is operably connected with the main transport lines for processing samples transported by the main transport lines.

15. The analytical system according to claim 10, wherein the bypass transport lines are located adjacent to the turntable.

16. The analytical system according to claim 10, wherein each of the bypass transport lines interconnects adjacent main transport lines.

17. The analytical system according to claim 10, wherein the turntable comprises a first rotatable transport line that transports the first sample racks and the second sample racks in a first direction and a second rotatable transport line that transports the first sample racks and the second sample racks in a direction opposite to the first direction.

18. The analytical system according to claim 10, wherein the main transport lines comprise one or more pairs of main transport lines, wherein each of the pairs of main transport lines comprises a first main transport line that transports the first sample racks and the second sample racks in a first direction and a second main transport line that transports the first sample racks and the second sample racks in an opposite direction to the first direction.

19. The analytical system according to claim 18, further comprising an interconnection transport line that interconnects the first main transport line and the second main transport line, wherein the interconnection transport line is operably coupled to at least one controllable main/main line switch that guides the second sample racks from the first main transport line to the second main transport line via the interconnection transport line or keeps the first sample racks and the second sample racks on the first main transport line or the second main transport line.

20. The analytical system according to claim 19, wherein the bypass transport lines and the interconnection transport line form a looped path of travel around the turntable.

* * * * *

UNITED STATES PATENT AND TRADEMARK OFFICE
CERTIFICATE OF CORRECTION

PATENT NO. : 8,894,928 B2
APPLICATION NO. : 13/302160
DATED : November 25, 2014
INVENTOR(S) : Joerg Haechler Page 1 of 2

It is certified that error appears in the above-identified patent and that said Letters Patent is hereby corrected as shown below:

In the Specification

Col. 4, Line 17,
"transport directions (both-way)." should read
--transport directions (both-ways).--;

Col. 7, Line 8,
"paired into a substantially parallel paths. Accordingly, each" should read
--paired into substantially parallel paths. Accordingly, each--;

Col. 7, Line 22,
"(both-way)." should read
--(both-ways).--;

Col. 7, Line 38,
"way). For example, the turntable 6 may include a driving" should read
--ways). For example, the turntable 6 may include a driving--;

Col. 8, Line 33,
"the first main transport line 8 the same pair of main transport" should read
--the first main transport line 8 of the same pair of main transport--;

Col. 8, Line 46,
"some embodiments, the both ends of the first main transport" should read
--some embodiments, both ends of the first main transport--;

Signed and Sealed this
Twenty-sixth Day of January, 2016

Michelle K. Lee
*Director of the United States Patent and Trademark Office*

CERTIFICATE OF CORRECTION (continued)
U.S. Pat. No. 8,894,928 B2

In the Claims

Col. 17, Claim 9, Line 29,
"keeps the first sample racks and the second sample racks on" should read
--keep the first sample racks and the second sample racks on--; and Col. 18, Claim 12, Line 35,
"connection transport line or to keeps the first sample racks and" should read
--connection transport line or to keep the first sample racks and--.